ns", Sci. Amer., 1974, pp. 56-63, 65-68.

United States Patent [19]

Brooks et al.

[11] 4,263,916
[45] Apr. 28, 1981

[54] IMAGE AVERAGING FOR ANGIOGRAPHY BY REGISTRATION AND COMBINATION OF SERIAL IMAGES

[75] Inventors: Samuel H. Brooks; Robert H. Selzer, both of Los Angeles; Donald W. Crawford, Long Beach; David H. Blankenhorn, Pasadena, all of Calif.

[73] Assignee: University of Southern California, Los Angeles, Calif.

[21] Appl. No.: 890,103

[22] Filed: Mar. 27, 1978

[51] Int. Cl.$^3$ .............................................. A61B 6/00
[52] U.S. Cl. ................................................... 128/654
[58] Field of Search ............ 128/2 A, 2.05 F, 2.05 V, 128/653, 663, 654; 250/320–321, 323

[56] References Cited

U.S. PATENT DOCUMENTS

| | | | |
|---|---|---|---|
| 3,499,146 | 3/1970 | Richards | 250/320 |
| 3,614,426 | 10/1971 | Donzelle | 250/323 |
| 3,742,236 | 6/1973 | Richards | 250/320 |
| 3,809,886 | 5/1974 | Cochran et al. | 250/323 |
| 3,818,220 | 6/1974 | Richards | 250/323 |
| 3,824,399 | 7/1974 | Bjork et al. | 250/336 |
| 3,894,181 | 7/1975 | Mistretto et al. | 178/6.8 X |
| 3,924,129 | 12/1975 | LeMay | 250/336 |
| 3,952,201 | 4/1976 | Hounsfield | 250/403 |
| 3,954,098 | 5/1976 | Dick et al. | 128/2.05 Z |
| 4,078,177 | 3/1978 | Tiemens | 250/323 |
| 4,101,961 | 7/1978 | Rieber | 364/417 |
| 4,111,191 | 9/1978 | Shaw | 128/2 A X |
| 4,137,775 | 2/1979 | LeMay | 128/2 V X |
| 4,182,311 | 1/1980 | Seppi et al. | 250/363 S |

FOREIGN PATENT DOCUMENTS

1265933  3/1972  United Kingdom .................... 250/323

OTHER PUBLICATIONS

Seward, J. B. et al., "Peripheral Venous Contrast Echocardiography", Amer. Jrnl. of Cardiology, vol. 39, Feb. 1977, pp. 202–212.
Andrews, H. C. et al., "Image Processing by Dig. Computer", IEEE Spectrum, Jul. 1972, pp. 20–32.
Gordon, R. et al., "Image Reconstruction from Projections", Sci. Amer., 1974, pp. 56–63, 65–68.
O'Reilly, R. J. et al., "Automatic Computer Analysis of Digital Dynamic Radionuclide Studies of the Cerebral Circulation", J. N. M. vol. 13, No. 9, Sep. 1972, pp. 658–666
Hoeffer, E. E., "Electronic Synthesis of Tomograms", Medicamundi, vol. 19, No. 2 (1974), pp. 66–67.
Kikuchi, Y. et al., "Ultrasono-Cardio-Tomography", Japan Electronic Engr., Oct. 1970, No. 7, pp. 53–60.
Kaneko, T., "St-line Approx. for Boundary of LV Chamber from a Cardiac Cineangiogram", IEEE BME, vol. 20, No. 6, Nov. 1973, pp. 413–416.
Marr, R. B. (ed.), "Techniques of 3-D Reconstruction", Proc. of Intnl. Workshop of Brookhaven Nat. Lab., Upton, N.Y., Jul. 16–19, 1974, pp. 99–106.
Greenleaf, J. F. et al., "Algeb. Reconst. of Spat. Distributions of Acoustic Velocities in Tissue from their TOF Profiles", Acoust. Holog., vol. 6, 1975, pp. 71–90.
Roth, W. et al., "Radiography by Electro-optical Means", Proc. of 7th Am. Biomed. Sci. Instr. Symp. on Imagery in Medicine, Ann Arbor, Mich., 19–22, May 1969, pp. 171–171.
Alpert, N. M. et al., "Non-Im. Nuclear Kinecardiography", JNM, vol. 15, No. 12, Dec. 1974, pp. 1182–1184.
Ellis, R., "Tracer Method Examines Human Blood Circ.", Nucleosis, p. 56, Jul. 1959.
Breckinridge, J. B., "Coherent Interferometer and Astronom. Applications", Applied Optics, vol. 11, No. 12, p. 2996, Dec. 1972.
"Two-Dimensional Whitelight Coherent Interoferometer", Applied Optics, vol. 13, No. 12, p. 2760, Dec. 1974.
Breckenridge, J. B., "Obtaining Information Through the Atom at the Diffract. Limit of a Large Aperture", Jrnl. of Opt. Soc. of Amer., vol. 63, No. 7, Jul. 1975.
Breckenridge, J. B., "Measurement of the Amplitude of Phase Excursions in the Earth's Atmosphere", Jrnl. of Opt. Soc. of Amer., vol. 66, No. 2, Feb. 1976.
Breckenridge, J. B., "Interfec. in Astron. Speckle Patterns", JOSA, vol. 66, No. 11, Nov. 1976.

*Primary Examiner*—Robert W. Michell
*Assistant Examiner*—Francis J. Jaworski
*Attorney, Agent, or Firm*—Nilsson, Robbins, Dalgarn, Berliner, Carson & Wurst

[57] ABSTRACT

A method and apparatus for angiography in which information contained within multiple serial images of contrast medium flowing through a blood vessel is combined to form a single image having improved vessel edge delineation. More specifically, a method is disclosed whereby a contrast medium opaque to X-rays is injected into a blood vessel distant from an artery section of interest, preferably injected into a vein, whereby the contrast medium is mixed with blood prior to its passing through the artery section. Multiple X-ray images are obtained as the contrast medium and blood mixture flows through the artery section. These multiple images are registered with respect to each other according to a landmark contained within the patient, the landmark having a predetermined relationship to the vessel of interest. The landmark could be a bone, catheter or any other material opaque to X-rays. Density measurements are made with respect to each corresponding image segment or element of the multiple images and are combined to synthesize a composite image. The synthesized image has an edge uncertainty equal to that of one of the individual images divided by the square root of the total number of images utilized.

29 Claims, 6 Drawing Figures

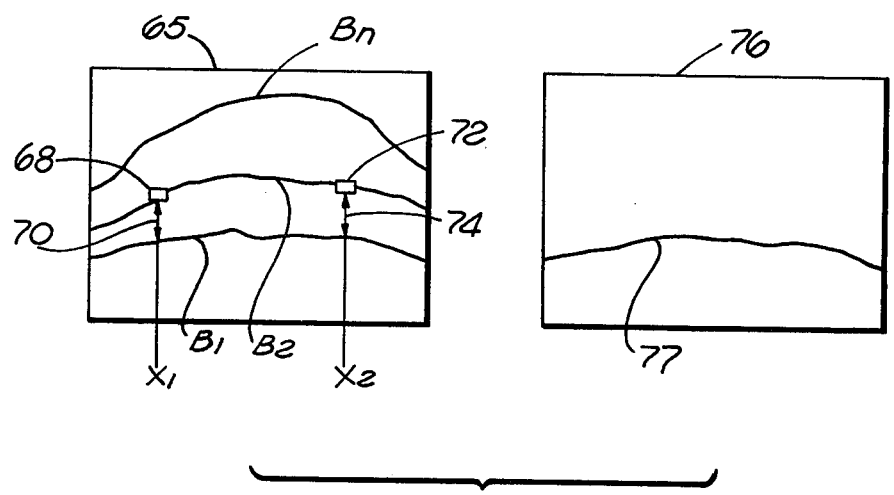
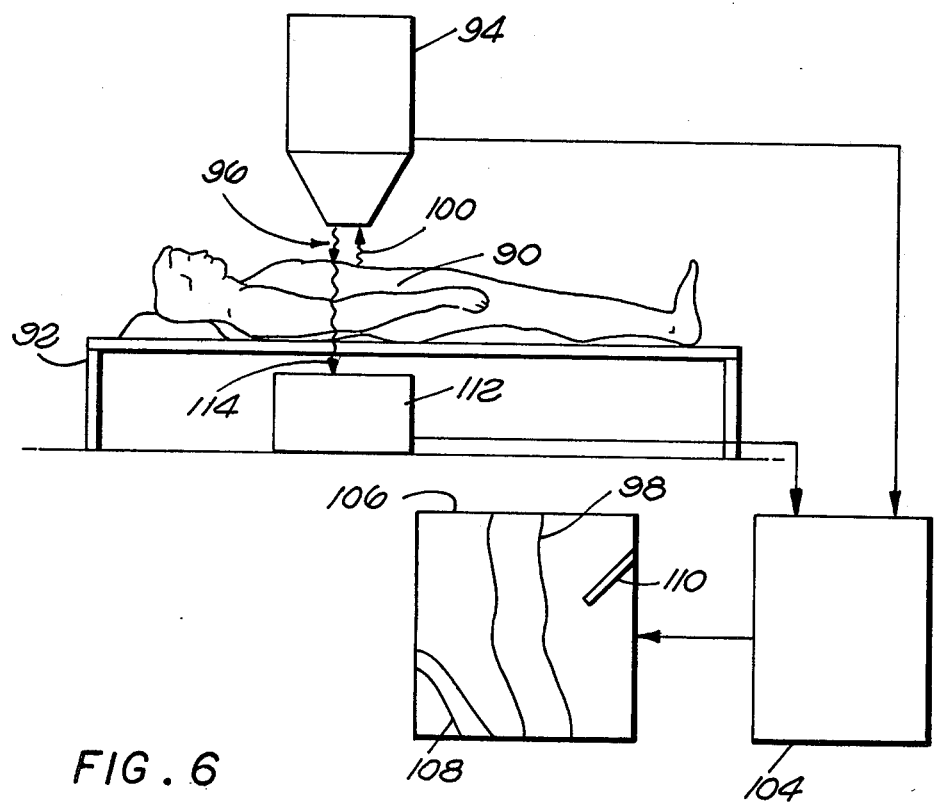
FIG. 5
FIG. 6

IMAGE AVERAGING FOR ANGIOGRAPHY BY REGISTRATION AND COMBINATION OF SERIAL IMAGES

FIELD OF THE INVENTION

The field of art to which the invention pertains includes apparatus and methods for arterial angiography in which a single composite image is constructed from information contained in multiple, serially obtained images.

BACKGROUND AND SUMMARY OF THE INVENTION

Arterial angiography as commonly practiced involves an arterial injection of a contrast medium opaque to X-rays and subsequent X-ray photography of the artery section of interest distal to be injection. In contrast to tomography, angiography is practiced by obtaining images along a fixed direction; that is, the source of X-rays (or corresponding ultrasonic equipment) is fixed as is the location of the image receptor. Additionally, the patient is relatively immobile so that the artery section is maintained at a substantially fixed location and at a substantially fixed rotational disposition. A single picture or series of pictures of the artery section is taken as the contrast medium flows therethrough. A large amount of contrast medium is required in order to provide sufficient contrast to highlight the artery edge profile in each picture. Injection of this large amount of contrast medium poses a significant risk of trauma or fatality. As an example, coronary angiography has a fatality risk of the order of 0.01 to 0.001. On the other hand, if the contrast medium is injected in a vein, there is much lower risk of adverse consequences of the order of 0.0001. However, the resulting X-ray image has low contrast because of mixture, thereby dilution, of the contrast medium with substantial amounts of blood by the time it reaches the artery of interest. This low contrast makes it difficult to precisely define the artery edge, thereby making it difficult for a skilled person to determine whether corrective therapy is appropriate.

The present invention discloses a method and apparatus which eliminates the above-described disadvantages of current angiography, angiography being defined as any method for visualizing a blood vessel, the edge or lumen usually being of interest. Specifically, one aspect of the invention utilizes venous injection of the contrast medium while still providing an image which has a contrast equal to or better than that of an image obtained after direct arterial injection of the contrast medium. The method according to the invention includes the steps of injecting a contrast medium so that it will mix with blood to flow through a vessel or artery section of interest, obtaining multiple images of the vessel section as the blood/contrast medium mixture flows therethrough, and synthesizing a single composite image of the vessel section from information contained in the multiple images. In specific embodiments of the invention, a constrast medium opaque to X-rays is utilized. The vessel is irradiated by an x-ray source, the rays passing therethrough forming an image on an appropriately positioned X-ray sensitive film/screen combination. The synthesizing step includes registering the multiple images from landmarks that are contained within the patient and that have a relationship to the vessel of interest, and identifying density indices of corresponding segments of the registered images. A single image having corresponding indices either averaged or cumulatively added is formed from the identified density indices. In one embodiment, when the vessel does not move, the synthesizing step can include manually overlapping and registering transparent image negatives so that one may look through the registered negatives to observe the artery edge. This embodiment can be utilized for only a limited number of negatives because their cumulative opaqueness will soon mask the detail required for vessel resolution. In a preferred embodiment, computer technology is utilized whereby each image segment or element is assigned a digital representation according to its average density, a synthesized image being formed by the computer based upon the density information of each corresponding image segment.

One may utilize an X-ray sensitive phosphor in lieu of the X-ray sensitive film/screen combination, the phosphor being electronically scanned and the resultant signal being used to drive a video display tube or converted to a digital format for computer storage and subsequent processing.

If the vessel is moving during the time interval during which the images are obtained, a method of synthesizing a composite image includes the steps of defining anticipated image profiles based upon average vessel edge profiles of healthy vessels. The anticipated profile for the vessel at rest, called a base profile, is defined. An anticipated profile for each of the subsequent images is then derived with respect to the base profile. For example, an image taken 1/6th of a second after the image corresponding to the base profile would have a profile which represents the anticipated position of the vessel edge 1/6th of a second after that of the vessel edge corresponding to the base profile. Each image segment associated with the second image is then corrected by an amount equal to the offset between the base profile and the anticipated vessel edge profile for that picture, the correction being made so as to ascertain the position of the vessel edge at the time of the base profile position. This process is repeated for each of the subsequent images, thereby providing images in which all of the vessel edges are corrected so that they correspond to the time of the base profile. This offsetting can be most efficiently accomplished by a computer. Once the corrected images are developed, a synthesized image can be obtained as explained above.

Although in the preferred embodiment multiple images are obtained using X-ray photography, other techniques for obtaining vessel edge profiles could also be utilized. According to another aspect of the invention, the images could be obtained by the use of ultrasonic diagnostic instruments which are capable of distinguishing one type of tissue characteristic from another, thereby eliminating any need for injection of a contrast medium. When sound travels through soft tissue it suffers attenuation which increases with frequency. The greater the attenuation, the higher the relative reduction in the high frequency components. Means for developing a pictorial representation of the attenuation and reduction in high frequency components are well known in the art and can provide an alternative method of obtaining multiple images of the vessel, the images obtained being processed in the same manner as the X-ray images described above.

BRIEF DESCRIPTION OF THE DRAWINGS

FIG. 5 are diagramatic representations showing a method of synthesizing a composite image of a vessel whose profile is changing as multiple X-ray images are being obtained; and FIG. 6 illustrates a third embodiment of the invention in which images are formed from reflected ultrasonic waves.

DETAILED DESCRIPTION

The invention provides an apparatus for and a method of arterial angiography in which a contrast medium is injected at a point distant from an artery or vessel of interest, the medium being mixed with blood prior to flowing through the vessel of interest. Multiple images are obtained of the vessel as the mixture of medium and blood flows therethrough. The multiple images are registered so that density image information from each can be combined into a single composite image having a vessel edge much more clearly defined than that of any of the multiple images. This more clearly defined vessel edge allows a skilled person to more accurately decide as to the advisability of corrective therapy.

Figure 1:
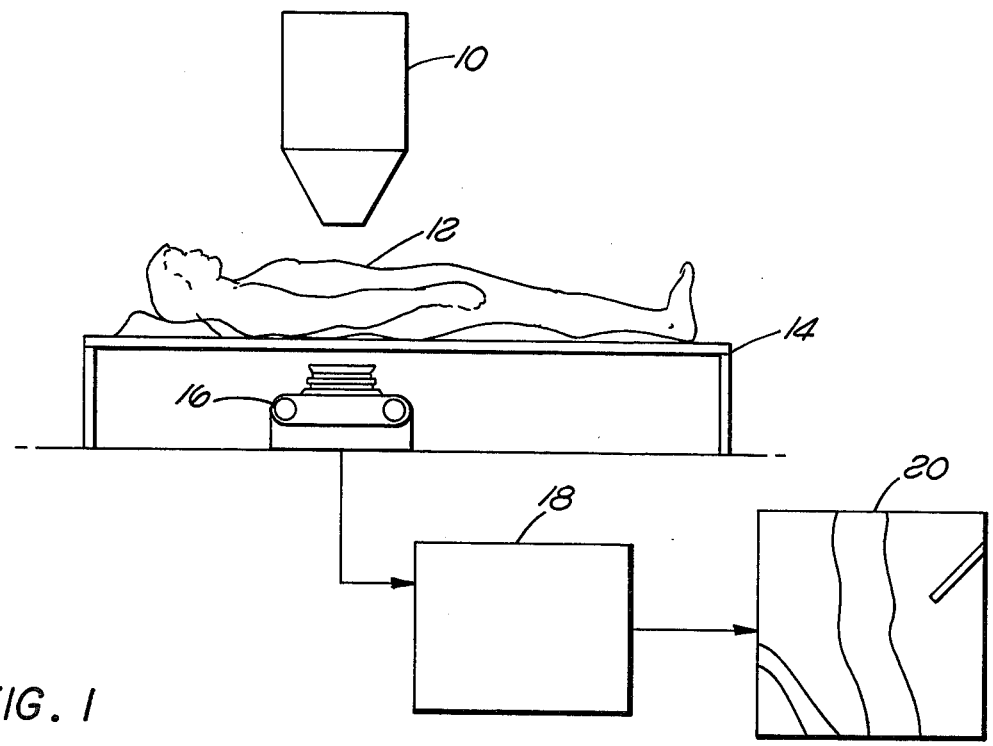
FIG. 1 is a perspective view showing the apparatus used in the present invention.

Referring to FIG. 1, the basic apparatus necessary of practice the teachings of the invention are shown. An X-ray source 10 is directed at a patient 12 resting on a table 14. Located directly beneath the patient is a medium sensitive to X-ray irradiation which in this first embodiment is an X-ray sensitive film/screen combination appropriately positioned within a camera 16. The camera 16 is adapted to take multiple images at a rate of approximately 6 frames per second although higher or lower rates can be utilized. Images obtained from the camera 16 are processed in a manner to be explained below by a processing means 18, the output of which is a single synthesized composite image 20 derived from all of the images obtained by the camera 16. Again it is emphasized that since the contrast medium has been injected at a point distant from to the vessel of interest, for reasons as explained above, any single image of the vessel having the contrast medium passing therethrough would have insufficient resolution to accurately determined location of a vessel edge. However, multiple images of the vessel obtained while it contains a diluted contrast medium, and thus a contrast medium concentration less likely to cause harm to the patient, can be combined to provide a composite image which will have the same or superior resolution with respect to images obtained from a more concentrated mixture of blood and contrast medium.

In one embodiment of the invention, image registration is effected by physically aligning each image according to a landmark or landmarks within the patient such as a bone, catheter, or any other item somewhat opaque to X-rays. The thus registered images will constitute a composite image having a resolution greater than that of any single image. This embodiment is limited to only a few images because the cumulative opaqueness of a large number of images will mask the detail necessary for proper vessel resolution.

Figure 2:
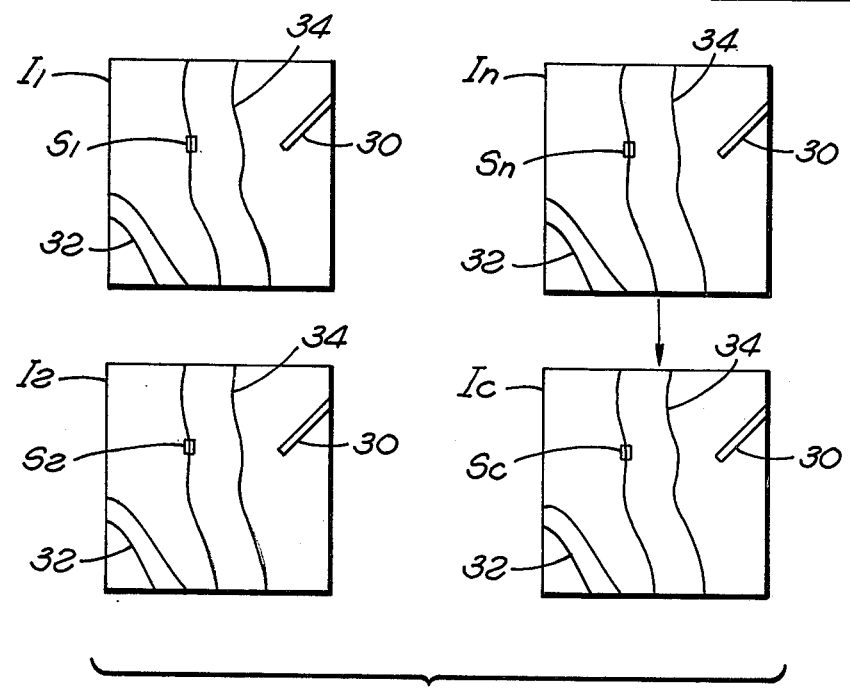
FIG. 2 are diagramatic representations showing development of a composite angiogram from a series of X-ray images.

Referring to FIG. 2, a series of X-ray images $I_1, I_2 \ldots I_n$ is obtained by the camera 16, the letter n representing the total number of images. It is important that each X-ray image have at least one registration landmark as above explained, the landmark having a predetermined relationship to the vessel section of interest so that slight movements by the patient and vessel which result in misregistration of the various images with respect to the vessel can be corrected. Referring to the first image $I_1$, two such means are shown, the first being a catheter 30 located within the patient's body and the second being a bone segment 32. Also shown is a somewhat indistinct vessel section 34, the edges of which are to be defined. Upon registration of the images $I_1$ through $I_n$, a composite image is derived as shown at $I_c$.

The composite image $I_c$ can be synthesized by many methods, all of which are diagramatically represented as the processing means 18 shown in FIG. 1. One method which can be used when the vessel is immobile is to manually overlap and register the transparent images $I_1$ through $I_n$ as previously described then view the composite image $I_c$ formed by the thus registered individual images. The viewing can be accomplished by back lighting the image array. To understand this method, and subsequent methods to be explained below, assume that each image $I_1$ through $I_n$ consists of a series of image segments or elements, one segment of which would be $S_1$ in image $I_1$, $S_2$ in image $I_2$ and $S_n$ in image $I_n$. Each segment $S_1$ through $S_N$ has a predetermined relationship to the landmarks, i.e. to the catheter 30 or the bone segments 32. The segment $S_c$ for the composite image $I_c$ has a density equal to the combined densities of its corresponding segments $S_1$ through $S_N$ of the series of images $I_1$ through $I_n$.

Figure 3:
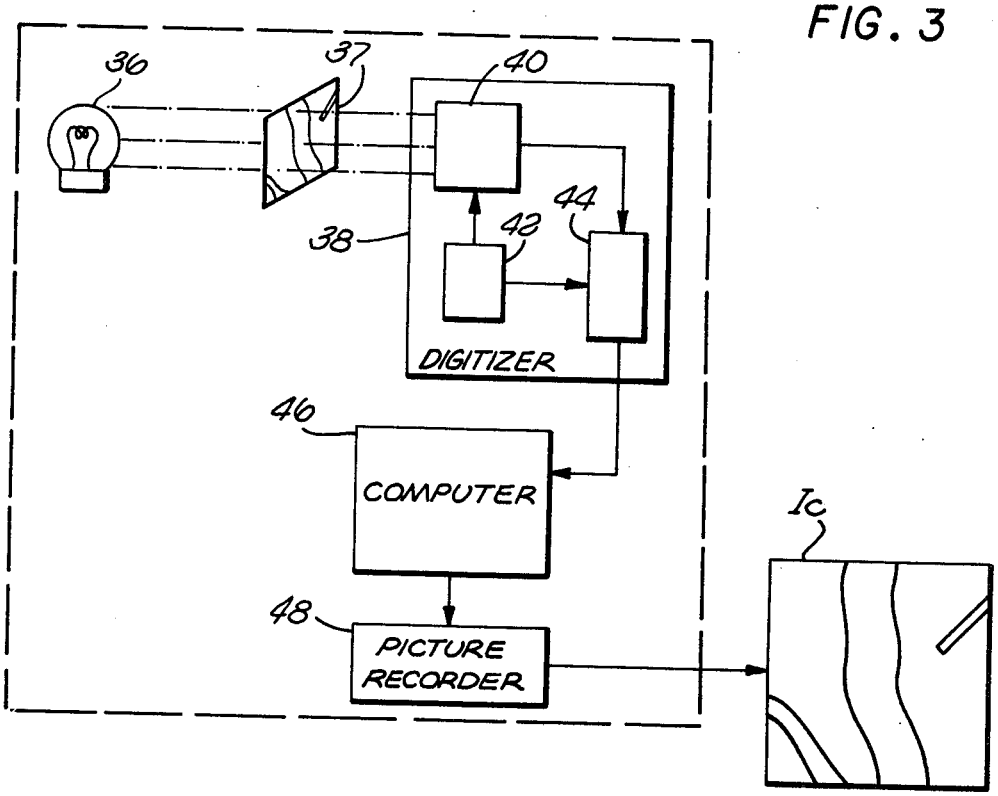
FIG. 3 is a diagramatic representation showing an embodiment utilizing a digital system to synthesize a composite image.

Another processing means 18 which can be employed is shown diagrammatically in FIG. 3 and consists of digitizing a density index associated with each image segment, and then combining the density indices of each corresponding image segment of each of the images $I_1$ through $I_n$ to develop a composite image $I_c$. Equipment to accomplish the above is well known in the digital processing art. Briefly, the system consists of a light source 36, the output of which is projected through one of the X-ray images $I_1$ through $I_n$, indicated at 37. A film digitizer 38, an example of which is a D57 digitizer made by Dicomed Corporation, converts the image into a series of digital words, each word corresponding to the density index of an image segment. The digitizer 38 consists of an electronic image disector camera 40, deflection and control circuits 42 and an analog to digital converter 44. The deflection and control circuits 42 control operation of both the image disector camera 40 and the analog to digital converter 44. The digital output of the film digitizer 38 is provided to a digital computer 46 and stored for subsequent processing. A computer which could be used for this purpose is the Digital Equipment Corporation PDP 11-45 although many other commercially available computers could also be utilized. After subsequent images $I_2$ through $I_n$ are digitized and stored in the computer 46, the computer can combine the corresponding image segment density information in any desired way, such as by addition or averaging, to derive a new density index for each picture segment. The output of the computer 46, which consists of these derived density indicies, is provided to a picture recorder 48 which in turn outputs a composite image $I_c$ based on the derived indices. As one can appreciate, the system above described can provide a composite image $I_c$ having each image segment corresponding to the average density of that segment in the preceding images $I_1$ through $I_n$, or a composite image having each image segment corresponding to a summation of the density information of that segment in the preceding image $I_1$ through $I_n$. All of the above described individual image processing method steps and apparatus components are well known in the digital processing art for other and diverse purposes.

Figure 4:
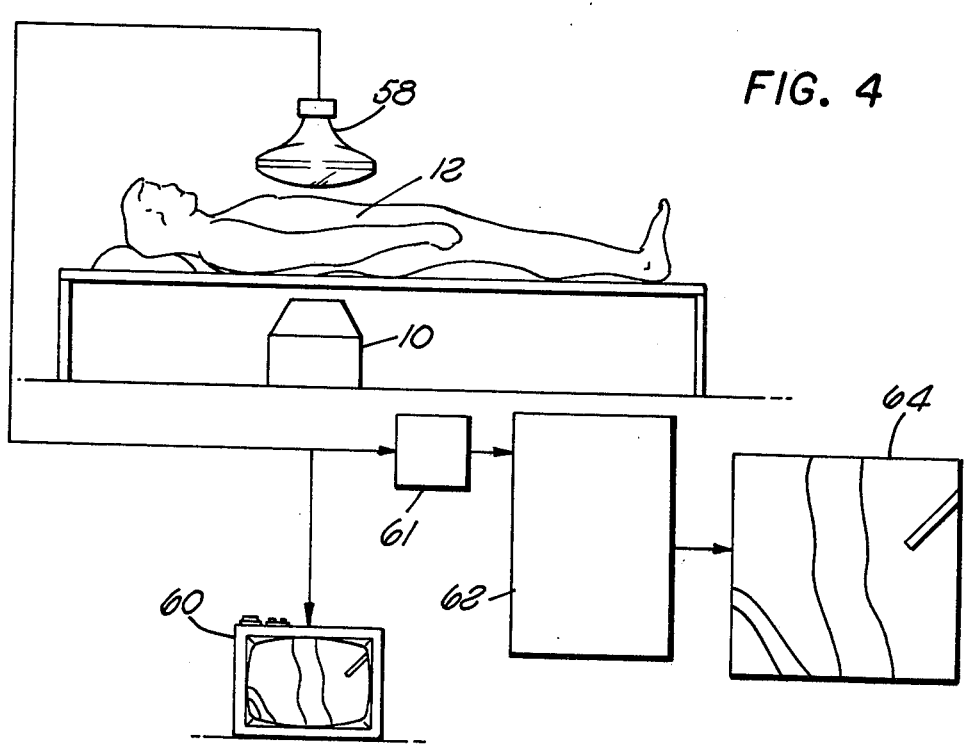
FIG. 4 illustrates a second embodiment of the invention in which images are formed on an X-ray responsive phosphor, the pattern of each phosphor image being electronically recorded, processed and displayed.

A further embodiment of the invention, shown in FIG. 4, utilizes the same X-ray source 10 of the first embodiment to irradiate a patient 12 laying on a table. However instead of the camera 16, the X-rays, after having passed through the patient 12, irradiate an X-ray sensitive phosphor contained within an image intensifier tube/scanner combination 58. If the vessel being X-rayed is relatively motionless, the output of the image intensifier tube/scanner combination 58 can be displayed by a video display unit 60 of the type that holds successive scans up to at least 30, thereby allowing a composite image $I_c$ to be developed as each subsequent image $I_2$ through $I_n$ is provided to the display unit 60. One example of such a video display unit is a Model 639 Scan Converter manufactured by Hughes Aircraft Company. Alternatively, the output of the image intensifier tube/scanner 58 can be providedd to an analog to digital converter 61, the output of which is provided to a digital computer 62 which can process information from the various images $I_1$ through $I_n$ as previously described to form a composite image $I_c$. The composite image can be displayed in many ways, one example of which would be by a standard television monitor 64.

Movement of the blood vessel during the image taking interval makes registration more difficult. One method of effecting registration, diagrammatically illustrated in FIG. 5, comprises establishing a base line position for the vessel edge, the base line $B_1$ corresponding to an anticipated vessel edge profile in the first image $I_1$. The base line $B_1$ can be manually defined by a skilled person. From this base line position $B_1$, an anticipated vessel edge position $B_2$ through $B_n$ for each of the subsequent images $I_2$ through $I_n$ is defined based upon knowledge as to the movement of an average vessel during the time interval between each image. Having established the anticipated profiles $B_1$ through $B_n$, one can derive an anticipated offset for the vessel edge off each image $I_2$ through $I_n$ with respect to the base profile $B_1$. Vessel edge profiles $B_1$ through $B_n$ which correspond to images $I_1$ through $I_n$ are shown in a vessel edge correction chart 65. Using the second image $I_2$ as an example, each segment of the image $I_2$ is offset by an amount equal to the anticipated offset $B_2-B_1$ of its vessel edge with respect to the base line profile $B_1$. Thus a first image segment 68 of the second image $I_2$ located along the abscissa at $x_1$, would be offset towards the base line $B_1$ by a first offset distance 70 equal to the value of $B_2-B_1$ at $X_1$. Similarly, a second image segment 72 located along the abscissa at $x_2$ would be offset towards the base line $B_1$ by a second offset distance 74 equal to the value of $B_2-B_1$ at $x_2$. After each of the images $I_2$ through $I_n$ are corrected in accordance with the above, a composite image $I_c$ shown at 76 and a composite vessel edge 77 are synthesized as previously explained. However, by using high-speed X-ray camera equipment currently available, movement of the vessel during the time interval over which the images are obtained will be small with respect to the allowable uncertainty in vessel edge location, thereby making the somewhat elaborate method described above less critical.

Utilizing the present invention, the estimated vessel edge finding error is quite low. This can be illustrated by an example in which 100 cc of Hypaque 75 M$^r$ (385 mg iodine/ml) is venously injected in the arm whereas the X-ray site is in the femoral artery. The estimated blood volume between the injection sight and the X-ray site is 1500 ml. For an injection duration of 4 seconds and an injection rate of 25 ml per second, it is estimated that peak concentration in the femoral artery to be X-rayed is 23.1 mg of iodine per ml of fluid present in the vessel. A concentration greater than 80% of the peak concentration, or 18.5 milligrams of iodine, will be present in the artery for five seconds. Thus 30 images of the artery can be taken utilizing a frame rate of 6 frames/second. The standard deviation of a vessel edge in a low-contrast image from which a skilled person can locate the artery edge is estimated to be 400 microns, whereas the standard deviation for 30 images combined as above-described is estimated to be 73 microns (400 divided by the square root of thirty). Thus one can appreciate that the invention teaches a method for obtaining a more precise definition of the artery edge without the high concentration contrast medium which would be required if the medium were injected directly into the artery of interest.

A second example utilizes a coronary artery as the X-ray site and as an injection site a distant pulmonary artery selected so that approximately 500 ml blood is contained between the injection site and the X-ray site. An injection of 100 cc's of Hypaque 75 M$^r$ during a 4 second interval results in a peak concentration in the coronary artery of 56.4 mg of iodine per ml of fluid. Concentrations exceeding 80 percent of this peak concentration will occur for 2.5 seconds, thereby allowing at a rate of 6 images per second or 15 images to obtained. The standard deviation of a single image in this instance would be 170 microns and the standard deviation of the 15 images when combined according to the principles of the invention will be 43.9 microns.

A third embodiment of the invention utilizes ultrasonic imaging as a non-invasive alternative to the injection of a contrast medium (e.g., indocyanine green dye, saline solution or blood, as referred to in "Peripheral Venous Contrast Echocardiography" by Seward et al, *The American Journal of Cardiology*, Vol. 39, Feb. 1977, pp. 202-212, at p. 210) into a patient, although a contrast medium could be utilized in conjunction with ultrasonic imaging. It is theorized that this method is most useful when the artery section of interest is within a few centimeters of the skin and is not obscured by bone or gaseous-containing structures. The carotid artery meets the above requirements and is medically significant because of the frequent build-up of atherosclerotic plaque. Instrumentation currently available is capable of producing an image of calcified plaque having a resolution of approximately 1 mm.

Referring to FIG. 6, a patient 90 is shown on a supporting table 92. An ultrasonic wave transmitter and receiver 94 is positioned so that radiating ultrasonic waves 96 will intersect an artery section of interest 98. The ultrasonic transmitter is chosen to radiate in the frequency range between 1 MHz and 10 MHz, although both higher and lower frequencies could also be utilized consistent with patient safety. The ultrasonic waves 100 reflected from the artery section of interest 98 are converted to an image by an the ultrasonic transmitter and receiver 94, many types of which are commercially available. Multiple images of the artery section are obtained and processed by a processing means 104 as previously described, the output being a composite image 106. A bone 108 or catheter 110 can be used for registration of the multiple images. Alternatively, a separate ultrasonic receiver 112 could be positioned below the patient 90 for conversion of the waves 114 passing through the patient 90 to an image to be supplied to the processing means 104.

We claim:

1. In a method of arterial angiography, in which an image of an artery section is obtained along a fixed direction with respect to said section, the steps comprising:
    injecting a contrast medium distant from an artery section of interest to mix with blood to flow through said artery section;
    thereafter sequentially obtaining multiple images of said artery section along said fixed direction;
    registering said multiple images in accordance with information contained in said multiple images;
    identifying corresponding image segments on each of said registered multiple images;
    determining the density of each identified image segment;
    combining said image segment densities of corresponding image segments into a single image segment; and
    constructing a composite single image of said artery section of interest from said combined image segment densities.

2. The method of claim 1 in which said contrast medium is venously injected.

3. The method of claim 1 or 2 in which said multiple images are obtained from X-rays passing through said artery section of interest.

4. The method of claim 1 or 2 in which said registering step is effected by aligning at least one landmark internal to a patient.

5. The method of claim 1 or 2 in which said combining step comprises averaging each of said identified corresponding image segment densities.

6. The method of claim 1 or 2 in which said combining step comprises adding each of said identified corresponding image segment densities.

7. The method of claim 1 or 2 in which said image segments are of an artery edge
    whereby a composite image of said artery edge is obtained as said single image.

8. The method of claim 1 in which said multiple images are derived from ultrasonic waves interacting with said artery section of interest.

9. In a method of arterial angiography in which an image of an artery section is obtained along a fixed direction with respect to said section, the steps comprising:
    injecting a contrast medium distant from an artery section of interest to mix with blood to flow through said artery section;
    thereafter sequentially obtaining multiple images of said artery section;
    obtaining anticipated time-position profiles of said artery section edges, one position profile being designated a base line profile, each subsequent position profile corresponding to a time of one of said multiple images;
    matching each of said multiple images to its corresponding anticipated artery edge profile;
    developing a second artery edge profile for each of said images, said second profile being offset from said anticipated profile by the offset between said anticipated profile and said base profile; and
    constructing a composite image of said artery edge from said second vessel edge profiles.

10. The method of claim 9 in which said developing step comprises:
    registering each of said multiple images according to at least one landmark internal to a patient;
    dividing each of said multiple images into a plurality of image segments; and
    offsetting each image segment by an amount equal to the distance between its anticipated position and said base line profile, all of the offset image segments comprising an image having an artery edge profile corrected for the anticipated movement of the artery edge in the time interval occurring between the base line profile and the time the image was attained.

11. In a method of arterial angiography in which an image of an artery section is obtained along a fixed direction with respect to said section, the steps comprising:
    injecting a contrast medium distant from an artery section of interest to mix with blood to flow through said artery section;
    thereafter sequentially obtaining multiple images of said artery section along said fixed direction as said contrast medium flows therethrough;
    registering said multiple images in accordance with information contained in said multiple images;
    identifying density indices of corresponding segments of said registered images; and
    forming a single image from said identified density indices, thereby more precisely defining edges of said artery section.

12. The method of claim 11 in which said contrast medium is venously injected.

13. The method of claim 11 or 12 in which said registering step comprises registering said multiple images in accordance with at least one landmark contained within a patient's body.

14. The method of claim 11 or 12 in which said multiple images are obtained from X-rays passing through said artery section.

15. The method of claim 14 in which said multiple images are obtained on an X-ray sensitive film/screen combination.

16. The method of claim 14 in which said multiple images are obtained on an X-ray responsive phosphor, the pattern of each image on said phosphor being electronically recorded.

17. In a method of arterial angiography in which an image of an artery section is obtained along a fixed direction with respect to said section, the steps comprising: directing ultrasonic waves to an artery section of interest;
    sequentially obtaining multiple images of said artery section derived from said ultrasonic waves interacting with said artery section; and registering said multiple images in accordance with information contained in said multiple images;

identifying corresponding image segments on each of said registered multiple images;

determining the density of each identified image segment;

combining said image segment densities of corresponding image segments into a single image segment; and constructing a composite single image of said artery section of interest from said combined image segment densities.

18. The method of claim 17 in which said multiple images are formed from ultrasonic waves being reflected from said artery section.

19. The method of claim 17 in which said multiple images are formed from ultrasonic waves passing through said artery section.

20. The method of any one of claims 17-19 in which said ultrasonic waves are within a frequency spectrum of 1 MHz to 10 MHz.

21. An apparatus for obtaining an angiogram of an artery section containing a contrast medium, comprising:

means for maintaining an artery section at a substantially fixed location and at a fixed rotational disposition;

an X-ray source;

first means for directing X-rays from said source to said artery section along a fixed direction;

means fixed relative to said first means for obtaining sequential multiple X-ray images of said artery section; and means for registering said multiple X-ray images according to a landmark contained within a patient's body and synthesizing from said multiple X-ray images a composite image of said artery section.

22. The apparatus of claim 21 in which said X-ray source is a single source.

23. An apparatus for obtaining an angiogram of an artery section, comprising:

means for maintaining an artery section at a substantially fixed location and at a substantially fixed rotational disposition;

first means for directing ultrasonic waves from said source for said artery section along a fixed direction;

means fixed relative to said first means for obtaining sequential multiple images of said artery section derived from said ultrasonic waves interacting with said artery section; and means for registering said multiple images according to a landmark contained in a patient's body and synthesizing from said multiple images a composite image of said artery section.

24. The apparatus of claim 22 in which said ultrasonic wave source is a single source.

25. The method of any one of claims 1, 9, 11 or 17 in which said images are obtained from a single exposure source.

26. In a method of arterial angiography, in which an image of an artery section is obtained along a fixed direction with respect to said section, the steps comprising:

injecting a contrast medium distant from an artery section of interest to mix with blood to flow through said artery section;

thereafter sequentially obtaining multiple images of said artery section along said fixed direction;

registering said multiple images by aligning at least one landmark internal to a patient;

identifying corresponding image segments on each of said registered multiple images;

determining the density of each identified image segment;

combining said image segment densities of corresponding image segments; and constructing a composite single image of said artery section of interest from said combined image segment densities.

27. In a method of arterial angiography in which an image of an artery section is obtained along a fixed direction with respect to said section, the steps comprising:

injecting a contrast medium distant from an artery section of interest to mix with blood to flow through said artery section;

thereafter sequentially obtaining multiple images of said artery section along said fixed direction as said contrast medium flows therethrough;

registering said multiple images in accordance with at least one landmark contained within a patient's body;

identifying density indices of corresponding segments of said registered images; and forming a single image from said identified density indices, thereby more precisely defining edges of said artery section.

28. The method of claim 26 or 27 in which said contrast medium is venously injected.

29. In a method of arterial angiography in which an image of an artery section is obtained along a fixed direction with respect to said section, the steps comprising:

directing ultrasonic waves to an artery section of interest;

sequentially obtaining multiple images of said artery section derived from said ultrasonic waves reflected from said artery section;

registering said multiple images;

identifying corresponding image segments on each of said registered multiple images;

determining the density of each identified image segment;

combining said image segment densities of corresponding image segments; and constructing a composite single image of said artery section of interest from said combined image segment densities.

* * * * *